US005811388A

United States Patent [19]
Friend et al.

[11] Patent Number: 5,811,388
[45] Date of Patent: Sep. 22, 1998

[54] DELIVERY OF DRUGS TO THE LOWER GI TRACT

[75] Inventors: David R. Friend, Menlo Park; David Wong, San Francisco, both of Calif.

[73] Assignee: Cibus Pharmaceutical, Inc., Burlingame, Calif.

[21] Appl. No.: 602,611

[22] Filed: Feb. 16, 1996

Related U.S. Application Data

[63] Continuation-in-part of Ser. No. 486,974, Jun. 7, 1995, Pat. No. 5,656,294.

[51] Int. Cl.$^6$ .............................. A61K 9/24; A61K 9/34; A61K 9/36; A61K 38/00

[52] U.S. Cl. .......................... 514/2; 424/85.1; 424/465; 424/474; 424/475; 424/479; 424/481; 424/485; 424/488; 514/3; 514/12; 514/21; 514/177; 514/178; 514/179; 514/180; 514/181; 514/182; 514/777; 514/780; 514/782; 514/960; 514/961

[58] Field of Search .............................. 514/2, 3, 12, 21, 514/177, 178, 179, 180, 181, 182, 960, 961, 777, 780, 782; 424/85.1, 452, 461, 465, 474, 475, 479, 481, 485, 488, 493, 496, 500

[56] References Cited

U.S. PATENT DOCUMENTS

| | | | |
|---|---|---|---|
| 3,629,393 | 12/1971 | Nakamoto et al. | 424/470 |
| 4,389,393 | 6/1983 | Schor et al. | 424/480 |
| 4,894,233 | 1/1990 | Sharma et al. | 424/440 |
| 4,994,276 | 2/1991 | Baichwal et al. | 424/440 |
| 4,999,200 | 3/1991 | Casillan | 424/480 |
| 5,108,758 | 4/1992 | Allwood et al. | 424/468 |
| 5,128,143 | 7/1992 | Baichwal et al. | 424/464 |
| 5,422,121 | 6/1995 | Lehmann et al. | 424/464 |
| 5,445,826 | 8/1995 | Kuhrts | 424/451 |
| 5,525,634 | 6/1996 | Sintov et al. | 514/777 |
| 5,656,294 | 8/1997 | Friend et al. | 424/465 |

FOREIGN PATENT DOCUMENTS

| | | |
|---|---|---|
| 2053569 | 4/1992 | Canada . |
| 0 343 993 A1 | 11/1989 | European Pat. Off. . |
| 0 371 493 A1 | 6/1990 | European Pat. Off. . |
| 0 481 240 A2 | 4/1992 | European Pat. Off. . |
| 0 485 840 A2 | 5/1992 | European Pat. Off. . |
| 2 667 242 | 4/1992 | France . |
| 2 238 243 | 5/1991 | United Kingdom . |
| WO 86/06627 | 11/1986 | WIPO . |
| WO 87/06241 | 10/1987 | WIPO . |
| WO 89/04673 | 6/1989 | WIPO . |
| WO 91/16881 | 11/1991 | WIPO . |
| WO 92/00732 | 1/1992 | WIPO . |

OTHER PUBLICATIONS

Adkin et al., "Colonic Transit of Different Sized Tablets in Healthy Subjects" *Journal of Controlled Release* (1993) 23:147–156.

Brondsted and Kopeck, "Hydrogels for Site–Specific Oral Drug Delivery: Synthesis and Characterization", *Biomaterials* (1991):584–592.

Cummings, "Short Chain Fatty Acids in the Human Colon", *Gut* (1981), 22:763–779.

Damgé et al., "New Approach for Oral Administration of Insulin With Polyalkylcyanoacrylate Nanocapsules as Drug Carrier" *Diabetes* (1968) 37:246–251.

Davis et al., "Transit of Pharmaceutical Dosage Forms Through the Small Intestine" *Gut* (1986) 27:886–892.

Feely et al., "Investigating the Gastrointestinal Transit of Controlled Release Mini–Matrices Using Gamma Scintiography", *Proceed. Intern. Symp. Control. Rel. Bioact. Mater.* (1985) 12:94–95.

Hardy et al., (1987) "Evaluation of an Enteric–Coated Delayed–Release 5–Aminosalicyclic Acid Tablet in Patients With Inflammatory Bowel Disease" *Aliment. Pharmacol. Therap.* (1987), 1:273–280.

Holt, et al., "Effect of Gel Fibre on Gastric Emptying and Absorption of Glucose and Paracetamol", *Lancet* (1979) 1:636–639.

Jain et al., "Controlled–Release Tablet Formulation of Isoniazid", *Pharmazie* (1992) 47:277–278.

Khosla et al., (1989) "Gastrointestinal Transit of Non–Disintegrating Tablets in Fed Subjects" *International Journal of Pharmaceutics* (1989) 53:107–117.

Kopecek, "Polymers for Colon–Specific Drug Delivery", *Journal of Controlled Release* (1992) 19:121–130.

Latymer et al., "Measurement of Transmit Time of Digesta Through Sections of Gastrointestinal Tract of Pigs Fed with Diets Containing Various Sources of Dietary Fibre (Non–Starch Polysaccharides)" *Arch. Anim. Nutr. Berlin* (1990) 40:667–680.

Marvola et al., "Gastrointestinal Transit and Concomitant Absorption of Verapamil from a Single–Unit Sustained–Release Tablet", *Drug Development and Industrial Pharmacy* (1987) 13(9–11):1593–1609.

Miranda et al., "High–Fiber Diets in the Treatment of Diabetes Mellitus" *Annals of Internal Medicine* (1978) 88:482–486.

Moore et al., "Absorption Enhancement of Growth Hormone from the Gastrointestinal Tract of Rats", *International Journal of Pharmaceutics* (1986) 34:35–43.

(List continued on next page.)

Primary Examiner—Jeffrey E. Russel
Attorney, Agent, or Firm—Cooley Godward LLP

[57] ABSTRACT

Pharmaceutical compositions for orally delivering a therapeutically effective amount of a drug to the colon without significant release of the drug in the upper GI tract after oral administration of the composition are described. The composition is a unit dosage in the form of a tablet that comprises about 0.01% by weight to about 10% by weight of the drug that is useful in treating a colonic disorder or that is absorbed from the colon; about 40% by weight to about 98% by weight of a hydrocolloid gum obtainable from higher plants; and about 2% by weight to about 50% by weight of a pharmaceutically acceptable binder. The compositions are useful for treating lower GI disorders in human subjects by administering a suitable amount to a subject in need thereof. A particularly preferred aspect is the process for preparing such composition in the form of a tablet.

30 Claims, No Drawings

OTHER PUBLICATIONS

McIntire et al., "Different Fibers Have Different Regional Effects on Luminal Contents of Rat Colon", *Gastroenterology* (1991) 101:1274–1281.

Price et al., "Characterization of Colonic Transit of Nondisintegrating Tablets in Healthy Subjects", *Digestive Diseases and Sciences,* (1993) 38(6) :1015–1021.

Price et al., "The Effect of Meal Composition on the Gastrocolonic Response: Implications for Drug Delivery to the Colon" *Pharmaceutical Research* (1993) 10(5):722–726.

Rubinstein and Gliko–Kabir, "Synthesis and Swelling Dependent Enzymatic Degradation of Borax Modified Guar Gum for Colonic Delivery Purposes" *S.T.P. Pharma Sciences* (1995) 5:41–46.

Sakr and Elsabbagh, "Effect of Particle Size Distribution on the Disintegrating Efficiency of Guar Gum" *Pharm. Ind.* (1976) 38(8) :732–734.

Salyers and Leedle, "Carbohydrate Metabolism in the Human Colon" *Human Intestinal Microflora in Health and Disease,* Chapter 6, pp. 129–146 (1983).

Spiller et al., "Emptying of the Terminal Ileum in Intact Humans: Influence of Meal Residue and Ileal Motility" *Gastroentrology* (1987) 92:724–729.

Trenev, "We Need Friendly Bacteria" *Total Health* (1988) 10:29–29.

Venter and Vorster, "Possible Metabolic Consequences of Fermentation in the Colon for Humans" *Medical Hypotheses* (1989) 29:161–166.

Waaler et al., "Biopharmaceutical Studies of Naftidrofuryl in Hydrocolloids Matrix Tablets" *International Journal of Pharmaceutics* (1992) 87:229–237.

Watanabe et al., "Factors Affecting Prednisolone Release from Hydrogels Prepared with Water–Soluble Dietary Fibers, Xanthan and Locust Bean Gums" *Chem. Pharm. Bull.* (1992) 40(2) :459–462.

Woodley, "Peptidase Activity in the G.I. Tract: Distribution Between Luminal Contents and Mucosal Tissue", *Proceed. Intern. Symp. Control. Rel. Bioct. Mater* (1991) 18:337–338.

Yoshikawa et al., "Comparison of Disapearance from Blood and Lymphatic Delivery of Human Fibroblast Interferon in Rat by Different Administration Route", *J. Pharmacobio–Dyn.* (1985) 8:206–210.

DELIVERY OF DRUGS TO THE LOWER GI TRACT

CROSS-REFERENCE TO RELATED CASES

This is a continuation-in-part application of U.S. patent application Ser. No. 08/486,974, filed Jun. 7, 1995 now U.S. Pat. No. 5,656,294.

INTRODUCTION

1. Technical Field

This invention relates to pharmaceutical compositions for oral administration to preferentially deliver drugs to the lower gastrointestinal (GI) tract, particularly to the colon.

2. Background

At the present time, there are no good orally-deliverable drug compositions that target treatment of various colon diseases such as chronic inflammatory diseases of the colon or diseases that require treatment by drugs that are better-absorbed through the colon than the stomach or upper GI tract. Also, there are no orally-deliverable drug compositions for peptides that release the peptides in a colonic environment where the peptides are not degraded to the same extent as peptides are degraded in the acid environment of the upper GI tract, particularly the stomach.

It is also known that peptides and proteins are large, molecules that are acid labile and polar to cause them to be poorly absorbed in the upper gastrointestinal tract. These molecules are degraded by luminal and brush border peptidases and generally have very short half-lives. As a result they have exceedingly low and variable bioavailability. Certain researchers have concluded that these molecules may be regionally absorbed in the colon. See, e.g., Moore, et al., Int. J. Pharm 34:35 (1986) discussing HGH and Yoshikawa, et al., J. Pharmacobiodyn. 8:291 (1985) discussing interferon. There is also evidence that there is much lower peptidase activity in the colon relative to the upper intestinal tract (Woodley, Proc. Int. Syn. Control. Rel. Bioact. Mat. 18:337 (1991).

Colon diseases include such conditions such as Crohn's disease, colitis (particularly ulcerative colitis), irritable bowel syndrome and the like. These diseases include a spectrum of inflammatory bowel disorders with overlapping clinical, epidemiologic and pathologic findings but without a definite etiology. Both Crohn's disease (CD) and ulcerative colitis (UC) are characterized by chronic inflammation at various sites of the GI tract, generally the colon (i.e., that part of the intestine from the cecum to the rectum). In treating these disease states, it is difficult to direct drugs that are specifically anti-inflammatory in nature and act topically to the desired site. For example, CD seems to affect the terminal ileum and the cecum primarily while UC seems to go past the second turn in the colon and affect the splenic flexure.

It One of the families of compounds that are used in the treatment of this family of diseases are glucocorticoids. These are thought to be useful in that the glucocorticoids have the capacity to prevent or suppress the development of the manifestations of this inflammation. The thought is that if the drugs can be administered to the inflamed area, the inflammation will recede and the body will ultimately be able to recover. Unfortunately, there are certain side effects the glucocorticoids exhibit if administered systemically and these side effects can be quite significant in treating any disease state. Another problem stemming from these side effects is that there is no way to deliver the drugs directly to the afflicted portion of the colon. Most of the oral formulations that are presently available disintegrate as they pass through the upper GI tract and thus, the steroids are absorbed into the body systemically and the subject being treated will experience some of the undesirable side effects.

The general approaches to delivering drugs to the lower GI tract (e.g. colon) include: 1) enteric coating designed to release drug in the more alkaline environment of the gastrointestinal tract, 2) bioerodible coatings and matrices, 3) prodrugs, 4) timed-release systems and, 5) enteric polymeric material-based release systems that release drug after they transit through the small and reach the large intestines. A general discussion of these approaches and others may be found in PCT Patent application No. PCT/US91/03014 by Sintov and Rubinstein.

It is known that certain hydrocolloids have a chemical structure that is subject to attack by the enzymes that are present in the colon and will cause the structure of the hydrocolloids to degrade and breakdown. Thus, it has been thought that if a composition could be prepared that would be made of a drug useful for treating the colonic condition that would pass through the upper GI tract without releasing the drug but would preferentially release it in the colon, the problem could be solved. Several attempts have been made to use a galactomannan-based composition (such as guar gum) to prepare compositions that are orally-administratable but which do not deliver a drug in the upper GI tract but instead make it through the tract to the colon. None of these have been entirely successful and some are more complex than desired. A paper by Rubinstein and Gilko-Kabir describes a borax-modified guar gum for colonic delivery purposes. However, that procedure requires that guar gum be chemically modified using borax (which is toxic at certain concentrations) in various concentrations to achieve the desired results. Other attempts have been made using glassy amylose to prepare compositions. These, too, were minimally successful. Still another approach requires that a galactomannan (locust bean gun) be mixed with an acrylate resin and coated around a drug-containing core (See U.S. Pat. No. 5,422,121).

It is also known that hydrocolloids that are obtainable from higher plants, such as guar gum, are used to increase the gastric residence time and provide sustained release of a drug which has the same bioavailability as the formulation of the drug. The concept is spelled out in co-pending application U.S. Ser. No. 08/348,515 filed Dec. 1, 1994 now abandoned. A broad range of hydrocolloid gum obtained from higher plants could be used to achieve those ends. The type of drug that could be used in the composition of that invention generally included nonpeptidic drug categories that exhibit a preferential window of absorption in the upper GI tract and/or that are generally susceptible to sustained release. Generally these drugs are present in high concentrations in the compositions.

It has now been discovered that drugs with high therapeutic activity (i.e., drugs that require less than about 10% weight in an orally-deliverable composition) can be delivered to the lower GI, particularly the colon. By carefully controlling the amount of a hydrocolloid that is obtainable from higher plants, such as guar gum, a composition is prepared for such drugs that is particularly useful for treating conditions of the lower intestinal tract, particularly chronic inflammatory diseases of the colon (and other colon disorders such as irritable bowel syndrome, constipation, diarrhea, etc.) and for delivering compounds (e.g. peptides) to the colon for better absorption. The families of compounds for which this is particularly valuable includes the glucocorticoids, local anesthetics, anticholenergics, 5-ASA, stimulant laxatives, peptides, certain antibodies and certain vaccines. While the amount of the hydrocolloid is one factor to consider in preparing the compositions of this invention, other important factors include the particle size of the hydrocolloid, the amount and type of other ingredients, the design of the tablet and other factors discussed herein.

OBJECTS OF THE INVENTION

An object of this invention is to provide a unit dosage composition comprising a drug useful for treating lower gastrointestinal disorders, particularly colonic disorders, that is orally-administered and delivers the major amount of the drug preferentially to, e.g. the colon of a human subject in need thereof.

Another object of this invention is to provide an orally-administered unit dosage composition comprising (a) a drug useful for treating lower gastrointestinal disorders, particularly colonic disorders, or (b) a drug that degrades in the upper GI tract, which composition goes through the upper GI tract without releasing significant quantities of the drug to a human subject being treated and releases the majority of the drug to the lower GI, e.g. colon.

Another object of this invention is to provide a unit dosage composition comprising a drug useful for treating lower gastrointestinal disorders, particularly colon disorders, that is orally-administered and minimizes adverse systemic effects to a human subject being treated.

Another object of this invention is to provide an orally-administered, unit dosage composition that delivers the major amount of the drug useful for topically treating colon disorders to the colon so the drug is released for topical treatment while minimizing systemic effects of such drug.

Another object of this invention is to provide an orally-administered, unit dosage composition that systemically delivers drugs, such as peptides, by absorption throughout the lower GI or colon.

Another object of this invention is to provide a method for treating a human subject through oral administration of a unit dosage composition that achieves the foregoing objects of this invention.

Still another object of this invention is to provide a process for preparing a unit dosage tablet composition suitable for oral administration that attains the foregoing objects of this invention.

Other objects of this invention will be apparent to one of ordinary skill by reading the following specification and claims.

SUMMARY OF THE INVENTION

One aspect of this invention is a powdered mixture useful for preparing a tablet for orally delivering a therapeutically effective amount of a drug to the lower GI tract, particularly the colon, without significant release of the drug in the upper GI tract after oral administration of the tablet, which composition comprises about 0.01% weight to about 10.0% by weight of such drug;

about 40% weight to about 98% by weight of a hydrocolloid gum obtainable from higher plants; and about 2.0% by weight to about 50% by weight of a pharmaceutically acceptable excipient, wherein said mixture is free of any enteric polymeric material or gas-forming excipients.

Another aspect of this invention is a pharmaceutical tablet having an inner composition optionally coated by a pharmaceutically-acceptable coating (preferably an enteric coating), said tablet designed for orally delivering a therapeutically effective amount of a drug to the lower GI tract, particularly the colon, without significant release of the drug in the upper GI tract after oral administration of the tablet, which inner composition of the tablet comprises about 0.01% weight to about 10.0% by weight of a drug useful for treating a lower GI tract disorder;

about 40% to about 98% by weight of a hydrocolloid gum obtainable from higher plants;

about 2% to about 50% by weight of a pharmaceutically acceptable excipient; and no enteric polymeric material or gas-forming excipients.

Another aspect of this invention is a method for treating a disorder of the lower GI tract, particularly the colon, in a human subject, which method comprises orally-administering to a human subject in need thereof a tablet described above.

Another aspect of this invention is a method for preferentially delivering a drug to the lower GI tract, particularly the colon, wherein such drug is susceptible to enzymatic degradation in the upper GI tract, which method comprises orally-administering to a human subject in need thereof a tablet described above.

Still another aspect of this invention is a process for preparing a composition in the form of a tablet suitable for oral administration to a human subject, wherein the tablet composition preferentially delivers a therapeutically effective amount of such drug to the lower GI tract, particularly the colon, without significant release of the drug in the upper GI tract, which process comprises (a) mixing about 0.5% weight to about 10.0% by weight of such drug with about 40% weight to about 98% by weight of a hydrocolloid gum obtainable from higher plant; and about 2% by weight to about 50% by weight of a pharmaceutically acceptable excipient to form a uniform mixture (b) forming a tablet; and (c) optionally coating the tablet.

Other aspects of the invention will be apparent to one of ordinary skill of the art upon reading the following specifications and claims.

DESCRIPTION OF SPECIFIC EMBODIMENTS

The compositions of this invention are based on the observation that by carefully controlling the percentage of a hydrocolloid obtainable from a higher plant at a very high level in an orally-administered dosage form and combining it with a suitable excipient and a particular family of drugs at low concentrations (i.e., less than about 10% by weight), a composition can be obtained which traverses the upper GI tract without releasing any significant amount of drug, but when it reaches the lower GI tract, e.g. the colon, the drug is preferentially released due at least in part to the action of the enzymatic environment in the lower GI tract that attacks the hydrocolloid to release the drug. The compositions and methods of this invention are of a delayed release nature (as compared to sustained or extended release) particularly useful for colonic delivery of glucocorticoids, as well as other drugs (e.g. peptides) that might be inactivated (e.g., enzymatically degraded) if released in the upper gastrointestinal tract. Thus, for purposes of this application a delayed release composition allows for the release of most of the active ingredient in the lower GI, particularly the colon without releasing any significant amount of the drug in the upper GI tract as the composition travels through the entire GI tract. This is different than a sustained release composition that releases the active on a regular (i.e. constant) basis throughout the GI. Generally, a relatively high percentage of the hydrocolloid gum obtainable from higher plants is present, namely at least 50% to about 98% (depending in part on the purity of the commercially-available gum), with a lesser amount of a pharmaceutically acceptable excipient that provides lubricating, binding and/or disintegrating capability for the composition as well as providing a minimal hardness for the tablet so that it can be prepared pharmaceutically. This amount is less than about 50% but more than about 2% by weight of the composition. The remainder is a drug present at a level that is therapeutically effective and depends on the relative activity of the drug and its interaction with the composition. The drug may be useful for treating conditions of the lower GI, particularly the colon (e.g., inflammatory diseases) or other conditions requiring drugs that are better absorbed from the colon.

The Compositions

One aspect of this invention is an orally-deliverable tablet having an inner composition optionally surrounded by a pharmaceutically-acceptable coating. The tablet preferentially delivers a therapeutically effective amount of a suitable drug to the lower GI, e.g. the colon, without significant release of the drug in the upper GI tract upon oral administration of the composition to a subject in need thereof. The inner composition of the tablet comprises about 0.01% weight to about 10.0% by weight of a suitable drug (e.g., for treating inflammatory colonic disorders); about 50% by weight to about 98% by weight of a hydrocolloid gum obtainable from higher plants; and about 2% by weight to about 50% by weight of a pharmaceutically acceptable excipient such as a binder. Other optional materials may be present that will assist in establishing the desired characteristics of the pharmaceutical composition. These include materials that may enhance absorption of the drug in the lower GI, may protect the drug against degradation, may prevent dissolution, and the like. Optionally surrounding the inner composition of the tablet is a coating that is preferably of enteric polymeric material.

The solid tablet of this invention is designed to take advantage of (1) the protective characteristics of the hydrocolloid obtainable from higher plants in the upper GI and (2) the disintegrative characteristics of the hydrocolloid in the lower GI. Thus, the inner composition of the tablet may be one of several designs: (a) it may be a matrix of a therapeutically effective amount of the active ingredient uniformly dispersed throughout in combination with a high percentage of the hydrocolloid and a generally lesser amount of other excipients; (b) it may have a core, in which the active ingredient is concentrated, surrounded by a layer of material that is free of the active ingredient and that has a high percentage of the hydrocolloid and a generally lesser amount of other excipients; (c) it may have a concentration gradient of the active ingredient such that there is a greater amount in the core of the tablet with lesser amounts in multiple layers surrounding the core and very little or no active ingredient in the outer layer. Whether the design of the tablet is that of (a), (b) or (c) above, the specificity for regional delivery to the lower GI, especially the colon, is enhanced by enterically coating the tablet with an appropriate enteric coating material.

The hydrocolloid that is used in the subject invention is a hydrocolloid that is obtainable from higher plants. By "higher plant" is meant an organism of the vegetable kingdom that lacks the power of locomotion, has cellulose cell walls, grows by synthesis of inorganic substances and includes the vascular plants (or tracheophytes) of the division Spermatophyta, particularly those of the class Angiospermae. The gums may be extracted from the roots, legumes, pods, berries, bark, etc. Thus, higher plants do not include algae, flagellates, bacteria, slime molds, fungi, mosses, ferns, horsetails and the like. Representative hydrocolloid gums obtainable from higher plants include guar gum, gum tragacanth, karaya gum (also referred to as kadaya gum) and locust bean gum (also referred to as carob). Others may be readily apparent to one of skill in the art. See, for example, "The Chemistry of Plant Gums and Mucilages" by Smith and Montgomery from ACS Monograph Series, No. 141, 1959, Reinhold Publishing Company and the 18th edition of the Merck Index. A particularly convenient and useful hydrocolloid is guar gum which is a neutral polysaccharide and consists of long galactomannan molecules with some side chain attachments. The hydrocolloids used in the subject invention generally have high viscosity exhibited upon hydration, are normally linear (at least about 50% by weight of the compound is the backbone chain), and will normally have high molecular weight, usually about $3 \times 10^5$ daltons, more usually greater than about $1 \times 10^6$ daltons. Generally, the hydrocolloid comes as a powdered hydrocolloid gum and exhibits a viscosity at a 1% concentration in a neutral aqueous solution of at least about 75 centipoise per second (cps) at 25° C. after 24 hours, using a Brookfield viscometer (model LDF) with a number 3 spindle at 90 rpms, preferably at least $1 \times 10^3$ cps and most preferably at least about $2 \times 10^3$ cps. Generally, the viscosity increases with increasing molecular weight. See Meer Corporation, "An Introduction to Polyhydrocolloids." Hydrocolloid gums most useful are those where the hydrocolloid is a polysaccharide hydrocolloid which is chemically designated as galactomannan. Galactomannans are polysaccharides consisting of long chains of $(1 \rightarrow 4)$ - β-D-mannopyranosyl units to which single unit side chains of α-D-galactopyranosyl are joined by $(1 \rightarrow 6)$ linkages. Galactomannans are found in a variety of plants but differ in molecular size and the number of D-galactosyl side chains. The galactomannans useful in this invention are commonly found in the endosperms of the leguminosae. Examples of the family of legumes are set forth in Table 1 which shows the family and the percent endosperm content of leguminous seeds.

TABLE 1

Estimated Endosperm Content of Leguminous Seeds

| Family | Endo-sperm % | Family | Endo-sperm % |
|---|---|---|---|
| Acacia | 1–15 | Glottidium | 2 |
| Astragalos | 2–3 | Glymnocladus | 15 |
| Baryxylum | 30 | Indigofera | 20 |
| Caesalpinia | 8–40 | Lespedeza | 1–4 |
| Cassia | 10–60 | Leucaena | 15 |
| Cercidium | 20 | Lotus | 2–4 |
| Ceratonia (carob) | 50 | Lysiloma | 4 |
| Chamaecrista | 8–15 | Melilotus | 8–12 |
| Colvillea | 30 | Mimosa | 3–30 |
| Crotalaria | 8–25 | Onomis | 25 |
| Cyamopsis (guar) | 50 | Parkinsonia | 25 |
| Cytisus | 15 | Parryella | 20 |
| Dalea | 20 | Prosopis | 15 |
| Daubentonia | 10–15 | Schrankia | 12 |
| Delonix | 25 | Sesbania | 20 |
| Desmanthus | 15 | Sophora | 20–25 |

TABLE 1-continued

Estimated Endosperm Content of Leguminous Seeds

| Family | Endo-sperm % | Family | Endo-sperm % |
|---|---|---|---|
| Desmodium | 2 | Trifolium | 3–10 |
| Gleditsia | 30 | Virgilia | 20 |

Table 2 shows the approximate composition of some galactomannans from legume seeds and the percentage of anhydromannose residues versus the anhydrogalactose residues. As can be seen from Table 2, the percentage of anhydromannose may vary from about 50% to about 90% (e.g. 86%) of the composition of the galactomannan with the percent anhydrogalactose varying from about 10% (e.g. 14%) to about 50%.

TABLE 2

Approximate Composition of Some Galactomannans from Legume Seeds

| Name of Seed | Anhydro-mannose % | Anhydro-galactose % |
|---|---|---|
| Caesalpinia spinosa (tara) | 71 | 26 |
| Caesalpinia cacalaco (huizache) | 69 | 28 |
| Ceratonia siliqua (carob, locust bean) | 80–86 | 20–14 |
| Cercidium torregyanum (palo verde) | 73 | 22 |
| Delonix regia (flame tree) | 79 | 19 |
| Cyamopsis tetragonolobus (guar) | 64 | 36 |
| Gleditsia triacanthos (honey locust) | 71 | 26 |
| Gymnocladus dioica (Kentucky coffee) | 71 | 26 |
| Sophora japonica | 81 | 16 |
| Desmanthus illinoensis (prairie-mimosa) | 70 | 26 |
| Indigofera hirsuta (indigo) | 72 | 23 |
| Cassia leptocarpa (senna) | 65 | 21 |
| Crotalaria intermedia (rattlebox) | 64 | 28 |
| Crotalaria juncea (rattlebox) | 60 | 40 |
| Crotalia striata (rattlebox) | 60 | 40 |
| Trigonella foenum graecum (fenugreek) | 52 | 48 |
| Medicago sativa (alfalfa) | 66 | 33 |

Preferably, the galactomannan that is most useful in this invention is derived from the cyamopsis tetragonolobus, commonly referred to as guar. This exhibits a percentage mannose residue of about 64% with a percent galactose residue of about 36%. Commercially available guar gum is about 66–82% galactomannan polysaccharide with impurities making up the remainder of the composition. According to the National Formulary (NF) standards the guar gum may contain up to 15% w water, up to 10% w protein, up to 7% w acid insoluble material and up to about 1.5% ash. Sources of commercially available guar gum are Aqualon Company, Wilmington, Del.; Meer Corporation, Cincinnati, Ohio; Stein Hall & Company; and TIC Gums, Inc., Belcamp, Md.

Other hydrocolloids may be readily apparent to one of skill in the art. See for example "The Chemistry of Plant Gums and Mucilages" by Smith and Montgomery from the A.C.S. Monograph series, #141, 1959, Reinhold Publishing Co. and the Eighteenth Edition of *The Merck Index*.

In general, the amount of the hydrocolloid that will be used is an amount that allows the composition to traverse the upper GI tract without significant disintegration and without releasing significant amounts of drug in the upper GI tract, i.e. to provide a delayed-release profile. A significant amount in this case is more than about 20%, thus more than about 80% of the drug will be released in the lower GI tract. Generally, that amount of hydrocolloid will be more than about 50% but less than about 98%. More preferably, the amount will be between about 60% to about 95% by weight of the hydrocolloid gum. Depending on individual variability, whether a subject has eaten or has fasted, and other factors, a tablet will traverse the stomach and upper intestinal tract in about 3 to 6 hours. During this time, little drug (less than 20%, preferably less than 10%) is released from the tablet of this invention. Once the tablet reaches the lower GI particularly the colon, the release of the drug is triggered by enzymatic degradation of the galactomannan gum. Once release is triggered, the release rate is relatively rapid for certain drugs, e.g., about 80–90% of the drug release occurs in about 2–4 hours or so, while other drugs such as steroids may be released over a longer period, e.g., about 6–10 hours.

This invention provides a vehicle for delivering drugs preferentially to the lower GI tract, especially the colon. Among the drugs for which this will be useful are drugs for the treatment of chronic diseases of the bowel, including inflammatory diseases. Generally, these drugs are highly active and require no more than about 10% by weight of total composition. These drugs may include certain glucocorticoids, local anesthetics, stimulant laxatives, peptides (both small and large), antibodies, vaccines, ACE inhibitors, anticholinergics, and other drugs such as diphenoxylate, loperamide, codeine, metronidazole, 5-amino salicylic acid (5-ASA), misoprostil, and sulfasalazine. Of these compounds, particularly valuable and therefore preferred are the glucocorticoids (also known as corticosteroids), particularly for treating inflammatory bowel diseases (IBD), which includes Crohn's disease and ulcerative colitis. These include hydrocortisone (and pharmaceutically-acceptable salts or esters such as the acetate, cypionate, sodium phosphate, sodium succinate, butyrate, valerate, etc.), beclomethasone, beclomethasone dipropionate, betamethasone (and its pharmaceutically-acceptable salts or esters such as the benzoate, dipropionate, sodium phosphate, acetate, valerate, etc.) cortisone, cortisone acetate, dexamethasone, dexamethasone acetate, dexamethasone sodium phosphate, flunisolide, methylprednisone, methylprednisone acetate, methylprednisone sodium succinate, paramethasone acetate, prednisolone, prednisolone acetate, prednisolone sodium phosphate, prednisolone tebutate, prednisone, triamcinolone, triamcinolone acetinide, triamcinolone diacetate, triacsinilone hexacetonide, alclometasone dipropioante, amcinonide, clobetasol propionate, clocortilone pivalate, desonide, desoximetasone, diflorasone diacetate, fluocinolone acetonide, fluocinonide, fluorometholone, flurandrenolide, halcinonide, medrysone, mometasone furoate, budesonide, fluticasone, tixicortol pivalate, prednisolone metasulfobenzoate, and the like. Other steroids may be apparent to one of ordinary skill in the art. The chemical names of these can be found at page 1451 of Goodman and Gillman's "The Pharmacological Basis of Therapeutics," 8th edition ("Goodman and Gillman") or in the Eleventh Edition of the Merck Index ("Merck"). Of these, dexamethasone, budesonide and fluticasone are preferred. In general, for glucocorticoids that are relatively water-insoluble, it is preferred that the particle size of the compound used be reduced to a very small size, particularly micronized. The particle size for micronized material is generally in the 1 to 10 micron range and may be obtained commercially from suppliers of the compound. Alternatively, the compound may be micronized using methods available in the art, such as those techniques found in *Remington's* at Chapter 88, which is incorporated herein by reference.

Local anesthetics that are useful in this invention include certain compounds that are set forth in Chapter 15 of Goodman and Gillman at pp. 311–331. These include procaine, cocaine, lidocaine, tetracaine, mepivacain, etidocaine, and the like.

Stimulant laxatives useful in this invention include, for example, docusate sodium, senna concentrates [sennosides], bisacodyl, potassium bitartrate, and the like.

Peptides that are useful in this invention include small peptides having a molecular weight about 2,000 or less, as well as larger peptides having a molecular weight of more than 2,000 and up to about 50,000 or more. Small peptides include LHRH or its derivatives (e.g., leuprolide, nafarelin, goserelin, deslorelin, historelin, buserelin and the like and the corresponding pharmaceutically acceptable acid addition salts such as the acetate, hydrochloride, etc.). Larger peptides that are useful in the composition of this invention include growth hormone, vasopressin and its analogs, calcitonin, insulin, glucagon, growth hormone releasing hormone (GHRH), relaxin, somatostatin, and cytokines or lymphokines such as tumor necrosis factor, erythropoietin, atrial natriuretic factor, cell growth stimulating factor (GCSF), $\alpha$, $\beta$ and $\gamma$ interferon, the interleukins, granulocyte colony stimulating factor, and the like.

Antibodies that can be delivered to the colon include IgG antibodies against toxins produced by C. difficile.

The particle size of the drug used in preparing the compositions of this invention may vary in size from about a tenth micron in size to more than 300 microns. It may also offer certain advantages to prepare microspheres (e.g. nanospheres or nanocapsules) of the peptides to aid in stabilizing and handling such compounds. For example, polyalkylcyanoacrylate nanocapsules with an average size of 220 nanometers (NM) may be prepared according to the method of Al Kouri, et al., *Int. J. Pharm.* 28:125432, 1986.

The percentage of the active drug that will be included in the composition will vary depending upon the activity of the drug relative to the condition being treated. In general, there will be no more than about 10%, preferably less than 5% of the active compound in the composition with a minimum amount of about 0.01% by weight. Preferably, the amount will vary between about 1% to about 4% by weight for glucocorticoids. For the highly active LHRH or its derivatives or larger peptidic molecules, generally the amount will be less than 1%. The amount of drug will depend on its activity, stability and other factors. For LHRH or its derivatives such as leuprolide, generally significantly more drug is needed than would be required for a parenteral injection. For example, a once daily dosage of leuprolide is 1 mg. Because of leuprolide's instability, even in the lower GI, 10 mg is needed to give similar bioavailability.

An important aspect of this invention is the weight ratio between the drug of the composition and the hydrocolloid gum. As discussed hereinbefore, there is a significantly greater amount of the hydrocolloid gum than of the drug. Generally, the weight ratio of hydrocolloid gum to drug will vary from about 9800:1 to about 4:1 depending on the potency of the drug and the amount of the hydrocolloid gum. For steroid drugs, the ratio will be in the range of about 65:1 to about 14:1. For drugs present in the composition at less than 1%, the ratio will be higher, e.g., 1000:1 or more to 100:1 or more.

Because of their size and polarity, peptides such as LHRH derivatives and larger proteins such as the interferons and human growth hormones are not entirely stable or well-absorbed, even in the lower intestinal tract such as in the colon. To assist in maintaining stability and in increasing the absorption of these compounds, a stabilizer and/or a penetration enhancer may be optionally included in the composition of this invention at a level that enhances stability and/or the rate of absorption in the lower GI tract. One stability enhancer that is particularly valuable for larger molecules is human serum albumin (HSA). Penetration (i.e., absorption) enhancers include compounds such as bile acids (as a sodium salt, e.g., sodium glycocholate, sodium dehydrodrocholate, sodium taurocholate), anionic detergents, (e.g., docusate sodium and sodium lauryl sulfate), non-ionic detergents (medium chain triglycerides, propylene glycol, polyethylene glycol, polyoxyethylene sorbitan fatty acid esters and the like), salicylates, acyl amino acids, acylcamnitines, lysolectin, and particulate carriers. Others may be apparent to one of skill in the art. Generally, such enhancer must be compatible with the other components of the composition and must not have adverse toxicological effects, i.e., it cannot irreversibly damage the intestinal musca. It is preferred that the enhancer be selected from those that are generally regarded as safe (GRAS) by the U.S. Food and Drug Administration (FDA).

In addition to the material set forth above as penetration enhancers, the LHRH compounds and larger compounds may also use certain enzyme inhibitors to further protect the peptidic molecules from degradation in the lower intestinal tract and in the colon. While the enzymatic environment in the lower intestinal tract and colon is less severe than in the upper intestinal tract, particularly the stomach, there are still enzymes in the lower intestinal tract that will relatively rapidly degrade the peptidic molecules. Thus the addition of enzyme inhibitors in the composition assists in protecting the peptidic molecules from degradation. Representative enzyme inhibitors include such things as polyacrylic acid (i.e., carboxypolymethylene referred to as the trademark CARBOPOL, for example CARBOPOL 934P) and the trademark CARBOMER (a cross-linked polymer of acrylic acid having a high molecular weight and containing about 56–68% of carboxylic acid groups), alginic acid (a hydrophilic colloidal carbohydrate extracted from various species of brown seaweeds), ethylenediaminetetraacetic acid (EDTA), cationic surfactants (for example, cetylpyridinium chloride), oleic acid and the like. Others may be apparent to one of skill in the art. Again it is preferable that the enhancer be selected from those that are generally regarded as safe (GRAS) by the U.S. FDA.

In preparing the compositions of this invention, the solubility and stability of the drug is taken into consideration. If the composition is a matrix tablet having the drug uniformly dispersed throughout the composition and the drug is less water soluble (e.g., a steroid), a lower percentage of the hydrocolloid is employed, e.g., about 50–75%. On the other hand, if the drug is highly water soluble, a higher percentage of the hydrocolloid is used, e.g., about 75–95% by weight. If an unstable, water-soluble drug is used (e.g., a small peptide or large protein), a composition of this invention having an active core surrounded by inactive material or having a concentration gradient may be desirable, as discussed hereafter.

While nearly every drug has a certain solubility in water, some are more soluble while others are less soluble. In determining such relative solubility, it is useful to refer some standard descriptive terms for solubility such as those provided in Chapter 16 of *Remington's*. These terms are set forth as follows:

| Descriptive Terms for Solubility | |
| --- | --- |
| Descriptive Terms | Parts of Solvent for 1 Part of Solute |
| Very soluble | Less than 1 |
| Freely soluble | From 1 to 10 |
| Soluble | From 10 to 30 |
| Sparingly soluble | From 30 to 100 |
| Slightly soluble | From 100 to 1000 |
| Very slightly soluble | From 1000 to 10,000 |
| Practically insoluble, or insoluble | More than 10,000 |

For purposes of providing guidelines for enabling one of skill in the art how to make and use the compositions of this invention those drugs that are generally sparingly soluble to very soluble should be considered "more water soluble" or "relatively water soluble," while those drugs that would be considered slightly soluble to insoluble should be considered "less water soluble" or "relatively water insoluble." These are not to be considered hard and fast restrictive rules, but simply guidance for one of ordinary skill.

One or more other excipients may be included in the composition of this invention to (1) impart satisfactory processing and compression characteristics to the composition (e.g., adjust the flowability, cohesion and other characteristics of the composition) and (2) give additional desirable physical characteristics to the tables (e.g. color, stability, hardness, disintegration). Mostly the excipients aid in the delayed release of the drug from the composition to achieve regional delivery to the lower GI. As used herein, the term "excipient" may include all excipients present in the dosage form, including all components other than the drug entity and the hydrocolloid gum from higher plants. A plurality of excipient substances may be present in any dosage form, and may include multiple substances having similar pharmaceutical function (e.g., lubricants, binders, diluents) or similar structure (e.g., a mixture of monosaccharides). Preferably the fewer excipients present the better. Such excipients are present in an amount sufficient to provide the composition with the desired delayed release/regional delivery characteristics, hardness rating and handling characteristics and will generally be present at a level of about 2% by weight to about 50% by weight, preferably about 2% by weight to about 40% by weight and more preferably about 2% to about 10% by weight. Excipients may be selected from many categories known in the pharmaceutical arts. The excipients used will be chosen to achieve the desired object of the invention keeping in mind the activity of the drug being used, as well as its physical and chemical characteristics such as water solubility and possible interactions with the excipients to be used. For example with drugs that are more water soluble, generally a lower percentage by weight of excipients will be used, i.e., less than about 20% or from about 2% to about 15% by weight, preferably no more than about 10% by wt, while for drugs that are less water soluble a higher percentage by weight may be used, e.g., about 20% up to about 40% by wt. These levels may be adjusted to achieve the desired hardness and porosity of the final tablet composition to obtain the delayed release profile.

Some of the excipients used in the composition of this invention may fulfill several roles, i.e., an excipient may act as a binder to aid in the delayed release/regional delivery profile while at the same time increasing the hardness characteristics of the composition (for better handling). Excipients that are useful for adjusting the hardness and porosity of tablet compositions of this invention include cellulosic derivatives, polyoxyethylene polymers of molecular weight (MW) from about 600,000 to about 8,000,000, colloidal silica, other natural hydrocolloid material (e.g., pectin), non-gas-forming mineral salts such as alkaline earth (e.g., $Ca^{+2}$, $Mg^{+2}$) phosphates and sulfates, and polyvinylpyrrolidone (PVP). Representative polyoxyethylene polymers are available under the tradename POLYOX® from Union Carbine Corporation. Examples include a POLYOX polymer of MW about 600,000 with a viscosity at 5% aqueous concentration of about 4500–8800 cps; a POLYOX polymer of MW about $4 \times 10^6$ with a viscosity of 1% aqueous concentration about 1500–4500 cps; and a POLYOX polymer of MW about $8 \times 10^6$ with a viscosity at 1% aqueous concentration of about $10-15 \times 10^3$ cps. Colloidal silica is available from W. R. Grace and Co. under the tradename SYLOID® 244FP. A useful mineral salt is EMCOMPRESS® brand of calcium phosphate. PVP (also referred to as povidone) is available under the tradenames PLASDONE® or POLYPLASDONE® (a cross-linked PVP) from ISP Technologies, Wayne, N.J. Representative cellulosic derivatives include hydroxypropylmethylcellulose [HPMC], microcrystalline cellulose [MC], hydroxypropyl cellulose [HPC], and ethylcellulose (EC). A representative commercial source for EC is Spectrum Chemical Mfg. Co., Gardena, Calif.; for HPMC is Dow Chemical Co., Midland, Mich. (under the tradename METHOCEL®); for HPC is Hercules Chemical Co., Wilmington, Del. (under the tradename KLUCEL®); and for MC is the FMC Corporation, Philadelphia, Pa. (under the tradename AVICEL®). Of these HPMC is preferred with METHOCEL premium, METHOCEL E3 and METHOCEL 50LV being particularly useful.

The combination of excipients such as the cellulosic derivatives, polyoxyethylene, colloidal silica and the like can be used to adjust the rate of hydration of the solid dosage formula, as well as allowing for a lower level of the powdered hydrocolloid gum obtainable from higher plants to be used, therefore, resulting in a less bulky tablet. In addition, combinations of the hydrocolloid gum with excipients may provide for greater degrees of control over drug delivery, but care must be taken in preparing the combinations, to avoid adverse effects. The adverse effects may include incomplete disintegration in the colon, dose-dumping, and the like. The amount and choice of the other excipient will also be affected by the other ingredients present in the formulation, so that one may modulate the effects of the other hydrocolloid by the other components.

To achieve the desired delayed release profile, an important consideration is the combination of a small amount of active agent with a particle size distribution of the hydrocolloid that is used in the composition of the invention. In general, the particle size distribution of the hydrocolloid, particularly guar gum, will be of such a size to provide a delayed release profile and will be of a median particle size less than about $150\mu$. Preferably, the size will be less than a median diameter size of about 125 microns ($\mu$) in diameter (120 standard sieve size), i.e. about 50% w of the particle mass will be below $125\mu$ and about 50% w will be above $125\mu$ it in diameter. In general the range will be from about $10\mu$ to about $125\mu$, preferably about 20 to $125\mu$. Smaller particles may be used, but are more difficult to handle. Preferably at least about 90% of the particle mass in the composition will be of a particle size less than $125\mu$. Sources of the hydrocolloid from higher plants are readily available commercially, but guar gum referred to as SUPERCOL® G3, having a particle size of about 75 to about 300 microns (where a little less than about 50% of the particle mass is smaller than about $150\mu$) is found to be useful particularly if the particle size is appropriately reduced. SUPERCOL® U, having a particle size from about 20 to about 100 microns, is particularly valuable. The SUPERCOL brand guar gum is available from the Aqualon Division of Hercules Corp., Wilmington, Del. Other sources include Henkel, a division of Emery Group, Cincinnati, Ohio, the Meer Corporation or TIC Gums, Inc. TICO-LV guar gum (having a molecular weight of about 300,000, a particle size distribution such that more than 99% of the particles are below 150μ in diameter, and a viscosity at 1% in water of about 75–100 cps) from TIC Gums, Inc. is also useful under certain conditions. Smaller particle sizes can be obtained by milling either SUPERCOL G3 or SUPERCOL U and sifting to get particles of the desired size. Generally the smaller the particle size within the range, the better the cohesiveness and the less drug is released in the upper GI. This is surprising in view of certain articles which suggest a smaller particle size results in a faster disintegration. (See for example an article entitled "Effect of Particle Size Distribution of the Disintegrating Efficiency of Guar Gum," by Sakr and Elsabbagh, *Pharm. Ind.* 38, NR8 (1976), pp. 732–734.) Conversely, the larger (or coarser) the particle size, the less cohesive is the composition and the more quickly the drug is released. The type and amount of other excipients will also affect the characteristics of the compositions of this invention. A more detailed discussion of the particular percentages is provided hereinafter. While not wishing to be bound by any particular theory, it is believed that the smaller particle size allows for a more rapid hydration of the dosage form surface, which retards further water penetration into the interior of the dosage form. This in combination with the small amount of drug provides a generally better delayed release profile.

The size distribution of the particles may be determined by standard sieve separation methods, i.e., by passing the guar particles through sieves having known mesh sizes (and known apertures) and collecting the retained or non-retained fractions. The same methods are useful for obtaining guar particles of desired sizes for use in preparing the composition of the invention.

From the foregoing discussion, it is seen that one aspect of this invention is a particle mass of a solid dosage form that can be administered orally as a tablet. Thus, the composition is neither a liquid nor a gas, but a solid tablet having an amount of drug as a unit dosage. Generally, this unit dosage will be an amount that can be swallowed by a human subject and may vary from a total of about 100 milligrams to about 1500 mg, preferably no more than about 1200 mg and particularly no more than about 800 mg. For children, the size of the tablet may be significantly less than for adults, and for elderly patients who have difficulty swallowing, the total amount may be less than what would be viewed as a normal amount for adults. It is to be understood that the tablets of this invention may be designed as a single tablet having a unit dosage amount or several smaller tablets, e.g. 2–5, may be combined in a capsule for oral administration. It is preferable that the composition used to prepare the tablet be granulated, as discussed hereinafter.

To ensure that the tablet composition of this invention exhibits the desired delayed release characteristics, it is important that certain materials be absent from the composition.

For example, previously, salts which form carbon dioxide in the gut, such as carbonates and bicarbonates, had been shown to be useful to disperse dosage forms with guar gum. Such mineral salts, such as the alkaline bicarbonates (e.g., sodium bicarbonate) must be excluded from compositions of this invention because it has been found that these salts tend to be difficult to process and store and tend to make the compositions disintegrate too rapidly. Therefore, such mineral salts that form a gas in the gastric juices are not present in the composition, i.e., the composition is free of these materials.

The inner composition which makes up the matrix of the tablet is also free of any enteric polymeric material. An enteric polymeric material is that material which is used to apply a film coating to a pharmaceutical product (e.g. a tablet) to protect the product from the effects of, or prevent the release of drugs in, the gastric environment. Such a coating material is referred as an "enteric coating." Enteric coatings are those which remain intact in the stomach, but will dissolve and release the contents of the dosage form once it reaches the small intestine. The purpose of an enteric coating is to delay the release of drugs which are inactivated by the stomach contents or may cause nausea or bleeding by irritating the gastric mucosa.

The action of enteric coatings results from a difference in composition of the respective gastric and intestinal environments in regard to pH and enzymatic properties. Although there have been repeated attempts to produce coatings which are subject to intestinal enzyme breakdown, this approach is not popular since enzymatic decomposition of the film is rather slow. Thus, most currently used enteric coatings are those which remain undissociated in the low pH environment of the stomach, but readily ionize when the pH rises to about 4 or 5. The most effective enteric polymers are polyacids having a $pK_a$ of 3 to 5. Although the pharmaceutical literature has contained references to many potentially suitable polymers (e.g. shellac) only three or four remain in use.

The most extensively used polymer is cellulose acetate phthalate (CAP) which is capable of functioning effectively as an enteric coating. However, a pH greater than 6 usually is required for solubility and thus a delay in drug release may ensue. It also is relatively permeable to moisture and gastric fluid compared to most enteric polymers. Thus it is susceptible to hydrolytic decomposition where phthalic and acetic acids are split off, resulting in a change in polymeric, and therefore enteric, properties. Another useful polymer is polyvinyl acetate phthalate (PVAP) which is less permeable to moisture and gastric fluid, more stable to hydrolysis and able to ionize at a lower pH, resulting in earlier release of actives in the duodenum. A more recently available polymer is hydroxypropyl methylcellulose phthalate. This has similar stability to PVAP and dissociates in the same pH range. A final example of currently used polymers are those based on methacrylic acid—methacrylic acid ester copolymers with acidic ionizable groups. These are represented by polymers having the tradename Eudragit available through Rohm Pharma. They have been reported to suffer from the disadvantage of having delayed breakdown even at relatively high pH.

Various systems recently have been introduced that allow each of these enteric polymers to be applied as aqueous dispersions, thus facilitating the use of aqueous film-coating technology for the enteric coating of pharmaceutical dosage forms. Generally, the enteric coating will be no more than about 0.5% by weight to about 10% by weight of the tablet having the composition of this invention.

In general, the composition of this invention having the hydrocolloid obtainable from higher plants will be free of any material that could be considered an enteric coating material, e.g., the inner composition will not have any enteric coating material mixed with the hydrocolloid material, whether the composition is a tablet having a uniform matrix, an active core, or a concentration gradient. This is because the enteric coating material would dissolve away in the upper GI, allow channeling and release the drug prior to reaching the lower GI or colon. Nonetheless, the tablets, once formed, may be coated with an enteric coating material as discussed hereafter.

As briefly discussed hereinbefore, the compositions of this invention may be one of several designs:

(a) A tablet which is a uniform matrix (the "uniform matrix tablet").

(b) A tablet having an active core surrounded by an inactive layer (the "active core tablet"—or "reservoir tablet").

(c) A tablet having a concentration gradient (the "concentration gradient tablet").

The processes for preparing each of these aspects of the invention, along with further compositional factors, will be discussed below. Whatever design is employed, the overall composition of ingredients will be within the approximate numerical limits set forth herein.

Process of Preparation

In preparing the tablet compositions of this invention one may use pharmaceutical compression or molding techniques, preferably the former due to its adaptability to large scale production methods. Using techniques known in the art, the tablets of the invention may take any appropriate shape such as discoid, round, oval, oblong, cylindrical, triangular, hexagonal, and the like. The tablets may be coated or uncoated. If coated they may be sugar-coated (to cover objectionable tastes or odors and to protect against oxidation), film coated (a thin film of water soluble matter for similar purposes), or enteric coated (to resist dissolution in gastric fluid but allow disintegration of the coating in the small intestine— as discussed hereinbefore). Depending on whether the tablet is a uniform matrix tablet, an active core tablet or a concentration gradient tablet, the process for preparation will vary slightly.

In order to ensure tablet hardness and uniformity of weight, content and other items, it is preferable to prepare the tablets having the composition of this invention by using a pre-granulation technique. In general the granulation techniques can include the wet granulation method, the fluid bed granulation method, the dry granulation method or direct compression. Each of these methods has certain advantages and disadvantages which are well recognized in the art. For example, the wet granulation has a greater probability that the granulation will meet all of the physical requirements for the compression of good tablets. However, its chief disadvantages are the number of separate steps involved and the time and labor necessary to carry out the procedure, particularly on a large scale. The fluid bed granulation method utilizes the concept of spraying a granulating solution onto suspended particles which are then dried rapidly in the suspended air. However, when the contents of the composition may be particularly sensitive to moisture or are unable to withstand elevated temperatures during drying, it may be better to use the dry granulation method and in this process slugging is used to form the granules. In each of these methods granules of the desired size are formed of the composition using the active and the hydrocolloid obtainable from higher plants having the desired particle size. Once the granules having the desired flow characteristics are obtained, a lubricant is added and mixed thoroughly with the resulting granules to form a composition which is then tableted by direct compression. The lubricant is necessary to ensure that the tablets are released from the compressor, the tableting machine or die. Further discussion of the granulation techniques as well as direct compression and other aspects of tableting are discussed at Chapter 89 of *Remington's*.

Once the tablets are appropriately formed they can then be coated by any of the necessary coating techniques as discussed in Chapter 90 of *Remington's*. For example, the tablets may be sugar-coated in accordance with the procedure discussed therein or film coated or preferably enterically coated. Enteric coating is preferred in the tablets of this invention to minimize the release of any of the drug in the upper GI and assure the release to the lower GI particularly the colon. As much as pertinent of the *Remington's* sections of Chapters 88 and 90 is incorporated herein by reference.

In general, a uniform matrix tablet is prepared using standard tableting techniques known to one of ordinary skill in the art such as those discussed in the 18th edition of "Remington's Pharmaceutical Sciences", Chapter 89, pp. 1633–1658 (Mach Publishing Company, 1990). In the simplest procedure, the ingredients (except for the lubricant) are simply blended together to provide a uniform mixture having the active ingredient uniformly dispersed throughout, the lubricant is then added and blended, and the tablets are compressed on an appropriate tableting machine.

Another aspect of this invention is the powdered mixture useful for preparing the inner composition of the tablet of this invention. The powdered mixture will vary slightly depending on how it is used in the preparation of the tablet. If the tablet design is a uniform matrix or a concentration gradient, the composition will generally be within the following parameters:

about 0.01% weight to about 10.0% by weight of the drug;

about 40% by weight to about 98% by weight of the hydrocolloid gum; and about 2% by weight to about 50% by weight of the pharmaceutically-acceptable excipient.

Of course the powdered mixture is free of any gas-forming salts or enteric polymeric material. If, on the other hand, the tablet design is an active core surrounded by the mixture of the gum and excipients, the composition will be about 40% to about 98% by weight of the hydrocofloid gum with remainder excipient. The active core may be prepared in any fashion in which the active drug is dispersed in an appropriate carrier then compressed to form such core. Suitable carriers include such material as sugars (i.e., lactose) and other pharmaceutically-acceptable carriers that do not interact with the drug.

If an active core surrounded by the hydrocolloid/excipient mixture is desired, a compression coating process is preferably employed to form the tablet.

Generally, the active core design is particularly useful for peptides such as LHRH and its derivatives. In this case, the peptide, its stabilizers (such as alginic acid, CARBOPOL934P or EDTA) and absorption enhancers are mixed with a suitable substance, e.g., lactose. Thereafter, the active core is surrounded by the hydrocolloid gum and other excipients using compression coating or other coating techniques generally known to one of skill in the art.

Compression coating is the compression of a dry coating around a tablet core involving the use of modified tableting machine. The finished product is a tablet within a tablet. The main advantage of compression coating is that it eliminates the use of any solvent whether aqueous or organic. Another advantage is that it provides a method to prepare active cores of water sensitive active agents. In compression coating, the inner tablet usually undergoes a light compression as each component is laid down, with the main compression being the final one. This technique may also be used to form a tablet having a concentration gradient where a higher percentage of active is in the core with a lesser percentage of active is in the outer layer.

The procedure includes first preparing a core tablet by mixing the active ingredient in combination with appropriate excipients such as lactose, Avicel PH-200 and a lubricant such as magnesium stearate and compressing the resultant mixture on a tablet press, e.g., using flat-faced punches (diameter 2–10 mm) on a Stokes B2 rotary tablet press. The weight and the hardness of the tablet is adjusted as required. The resulting tablet is then compression coated using the appropriately sized concave punch, e.g., about 5 mm to about 15 mm. About one third of the inactive coating is then placed in the die, the active core is placed on top of the to-be coating. The remaining two-thirds of the coating material is added along side and on top of the active core. The tablet is then compressed.

Another aspect of this invention is a process for preparing a composition in the form of a tablet suitable for oral administration to a human subject. As discussed hereinbefore, the tablet composition preferentially delivers a therapeutically effective amount of a drug to the lower GI tract, particularly the colon, without significant release of the drug in the upper GI tract. One process aspect of this invention comprises mixing about 0.01% by weight to about 10.0% by weight of a (a) drug useful in treating lower GI tract or colonic disorders or (b) a drug which is better absorbed from the lower GI tract or colon than the upper GI tract with about 40% by weight to about 98% by weight of a hydrocolloid gum obtainable from a higher plant; and about 2% by weight to about 50% by weight of a pharmaceutically-acceptable excipient to form a uniform mixture. The uniform mixture is then formed into a tablet and optionally coated with a suitable coating material. In the process, it is preferred that the median particle size of the hydrocolloid gum is about 150 microns or less. It is also preferred that prior to forming the tablet, the mixture is granulated by either a dry granulation method or a wet granulation method. These two methods of dry granulation or wet granulation, are spelled out in *Remington's* in chapter 88. In general, in the wet granulation procedure, the hydrocolloid of the appropriate particle size is mixed with a solution of an excipient and the active ingredient. This procedure is particularly good for corticosteroids such as dexamethasone or budesonide. The solvents for the excipient active ingredient may be any suitable solvent but ethanol is found to be particularly useful. The solution of active ingredient and excipient is added to the hydrocolloid very slowly over a period of time to form a uniform mixture of wet granules which are passed through an appropriate mesh size screen and dried. Generally, the size screen that is used is a rather large mesh such as a number 18 size to give large wet particles.

After the large wet particles are dried, the dried granules are passed through a screen with mesh size which creates smaller sizes. These resulting granules are then mixed with a suitable lubricant such as magnesium stearate and another excipient, preferable HPMC, and thoroughly mixed then compressed into tablets. By varying the amount of solvent, the time to equilibrium with room humidity and granule size, etc., the tablets can be designed to release at different rates and at different positions in the colon. Generally, it is preferable that the solvent used to form the granules initially be a non-solvent for guar gum. For this reason ethanol is preferred.

In general, when a larger amount of solvent is used relative to guar gum, the size of the resulting granules generally increases. In general, the hardness of tablets made by the wet granulation method is improved by decreasing particle sizes of the granules. This is thought to be true because more particle bonds formed with smaller particles due to the larger total surface area. The hardness also may be improved by the presence of moisture due to the plasticization effect of water on the polymer.

A non-solvent such as ethanol in the process may result then in softer tablets. Softer tablets would lead to a faster disintegration in the upper GI tract. In general, for the treatment of ascending colonic ulcer, compressing tablets with smaller granules that use less ethanol in the wet granulation process would be preferred. On the other hand, for diseases located at the descending colon, one would generally use more of the non-solvent such as ethanol in the wet granulation process and compress tablets with larger granules to retard the onset of fast drug release.

Administration

In general the tablets of this invention will be administered orally to a mammalian subject in need thereof using a level of drug that is sufficient to provide the desired physiological effect. The mammalian subject may be a domestic animal or pet but preferably is a human subject. The level of drug needed to give the desired physiological result is readily determined by one of ordinary skill in the art by referring to standard texts such as Goodman and Gillman and the Physician's Desk Reference. For orally delivered steroids the amount administered using a composition of this invention will be significantly less than that used for a standard formulation because the drug will be released preferentially to the lower GI (e.g., the colon) and will not be released to any significant extent in the upper GI. On the other hand, for large and small peptide or protein molecules, a larger amount will be needed for a composition of this invention than would be delivered on a daily basis by intramuscular, subcutaneous depot, or the like. For example, the daily amount delivered would be up to about ten times the amount delivered by the other known, non-oral detivert means.

The following examples are given to further explain the invention and to give specific examples of how to make and use the invention. However, they should be considered as exemplary only and not limiting in interpreting the scope of the claims. Throughout the specification, any and all references to a publicly available documents are incorporated into this patent application by reference.

EXAMPLES

Example 1

This example sets forth certain compositions of this invention in which the active ingredient is dexamethasone. The example provides guidance for showing whether a composition will meet certain objects of the invention.

A series of guar-based tablets designed to achieve differing profiles for the release of dexamethasone in the gastrointestinal tract were prepared. Formulations were selected on the basis of preliminary studies of the effects of excipients on tablet hardness and integrity in dissolution medium. Four dosage forms were chosen and tested in a three-part in vitro dissolution system. Three of these dosage forms represent compositions of this invention and target drug release preferentially to the colon. The fourth, fast-releasing dosage form was shown to release almost its entire drug load in the gastric fluid of the stomach for comparative purposes.

Tablet Ingredients

Avicel PH200 (microcrystalline cellulose) was purchased from FMC Corporation. Methocel E50LV and E3 (HPMC) were obtained from Dow Corporation. USP grade, micronized dexamethasone was purchased from Upjohn Company. Encompress (dicalcium phosphate) as purchased from Mendell. Magnesium stearate was obtained from Whittaker, Clark & Daniels. Coarse grade (G3) and fine grade (U) guar gum were purchased from Aqualon.

Powder Mixing and Tablet Preparation

For the small initial batches (i.e., 20 g), powders were generally mixed simply by spatulation before tableting. When larger batches were required (i.e., 150 g), powder ingredients (except magnesium stearate) were first sieved (mesh # 40) and mixed with spatulation method, then with a V-blender for 10 minutes. Magnesium stearate, as a lubricant for tableting, was added and the final powder mixture was blended for another 10 minutes.

All powders (except dexamethasone) for the dosage forms used in this Example 1 were passed through 40 mesh size sieve. Dexamethasone was then pre-mixed with approximately one-sixth of total guar gum powder by spatulation to obtain uniformity of drug content.

The tablets were manually compressed with a rotary tableting machine [Model dual pressure press, F. J. Strokes Machine Company, Philadelphia, Pa., with punches (Cups: concave, shallow, monoradius, diameter of 13/32")]. The tablets weighed ~300–350 mg each and contained approximately 9–13 mg drug to give a final concentration of 3% by weight. The formulations of the four selected formulations are:

A. 60.5% G3-grade guar, 36% HPMC E3, 3 % Dex, 0.5% Mg Stearate
B. 60.5% G3-grade guar, 36% HPMC E50LV, 3% Dex, 0.5% Mg Stearate
C. 24.5% G3-grade guar, 72% Avicel, 3% Dex, 0.5% Mg Stearate
D. 60.5% U-grade guar, 36% EMCOMPRESS, 3% Dex, 0.5% Mg Stearate Formulations A, B and D are representative of the invention.

Measurement of Physical Characteristics

1. Tablet Hardness

The hardness test for tablets was performed by Vanderkamp VK 200 Tablet Hardness Tester (VanKel Industries, Inc., Edison, N.H.). A tablet was placed at the strain gauge. As the moving jaw pressed the tablet against it, the force was recorded at the movement the initial fracture was detected.

2. Material Lost

Tablets were weighed before (a) and after (b) dissolution. Then, they were dried at 60° C. They were weighed again (c). To determine the amount of material lost, the following calculations were performed:

1. The weight of tablets was measured before (a) and after (b) the dissolution.
2. The tablets were dried and weighed (c).
3. The amount of material lost =a-c; the amount of water absorbed % w/w=(b-a)/c*100%.

3. Friability

The friability test for tablets was performed by Tablet Friabilater (VanKel Industries, Inc., Edison, N.H.). Approximately 4 g ($w_o$) of dedusted tablets were subjected to 100 free falls of 6 inches in a rotating drum at 25 rpm and were then reweighed (w). The friability, f, was found by using the formula:

$$f=100*(1-w_o/w)$$

Values of f from 0.8 to 1.0% were regarded as the upper limit of acceptability.

Dissolution Testing

1. Preparation of simulated gastric fluid (SGF)

Sodium chloride (7 g) and pepsin (11.2 g) were co-dissolved in 24.5 ml of hydrochloric acid. Deionized water was added to make the final volume equal to 3500 ml.

2. Preparation of simulated intestinal fluid (SIF)

Monobasic potassium phosphate (23.8 g) was dissolved in 875 ml of water. Sodium hydroxide (665 ml, 0.2N) and 1400 ml of water were then added. Pancreatin (35 g) was added and the resulting solution was adjusted with 0.2N sodium hydroxide to a pH of 7.5±0.5. The solution was subsequently diluted with water to a final volume of 3500 ml.

3. Preparation of simulated colonic fluid (SCF)

SCF was comprised of homogenized stool samples from healthy volunteers or from colitis patients (specimens homogenized if not sufficiently fluid). Preparations were used undiluted.

4. Dissolution Testing

Tablets were weighed and placed in 500 ml of simulated gastric fluid (SGF) for 2 hours with stir speed set at 50 rpm (USP method 2; paddle). Samples (5 ml) were taken at specified intervals for analysis of drug content and replaced with fresh medium. For testing drug release in SIF, tablets were subsequently transferred using an aluminum dish into vessels containing 500 ml of SIF (USP method 2; paddle). During transfer, the fluid was removed carefully by tilting the dish. Tablets were immersed in SIF for a period of 4 hours and stirred at a speed of 50 rpm. During this period, 5 ml samples were collected at specific time points and replaced with fresh medium. For further dissolution testing in colonic fluids, the tablets were then transferred into 10 g of SCF. The medium was mixed by dipping a plunger up and down 8 to 9 times per minute inside the test tube. Samples (0.5 g) were taken at specific intervals over an 18 hour period without replacement of the colonic medium. The temperature was maintained at 37° C. throughout the experiment.

Quantitative Analysis

Quantitation was done by averaged single point internal standard calibration. A standard solution containing 50 $\mu$g/ml dexamethasone (Dex) and 50 $\mu$g/ml triamcinolone acetonide (TrAce) was prepared. The standard mixture was injected before and after every 20 sample injections. The respective standard and internal standard peak areas were then averaged for use as the single point calibration factor. Calibration curves were previously generated for both Dex and TrAce. The respective curves were determined to be linear and went through zero. The standards were thus considered suitable for single point calibration.

All of the sample amounts were carefully measured (by mass or volume) and then spiked with 30 $\mu$l of a 1 mg/ml Dex/TrAce mixture. The spike is equal to 30 $\mu$g each of Dex and TrAce. After the samples were prepared (according to the descriptions in following sections) they were injected onto the HPLC column. The resulting concentrations of Dex and TrAce were calculated from the respective standards as such:

$$C_{smp}=C_{std}(A_{smp} \div A_{std}) \quad (1)$$

Where:
$C_{smp}$=concentration of the sample
$C_{std}$=concentration of the standard
$A_{smp}$=area of the sample
$A_{std}$=area of the standard The original concentration of Dex in the sample was then calculated as follows:

$$X=[(M*t/T)-d]/Z \quad (2)$$

Where:
X=concentration of Dex
M=measured concentration of Dex from equ 1
T=measured concentration of TrAce from equ 2
t=mass (in µg) of TrAce spiked into the sample
d=mass (in µg) of Dex spiked into the sample
Z=sample amount (mg or ml)

Samples were analyzed by HPLC for quantitation of dexamethasone released. The results were expressed as percent drug released relative to the amount in the intact tablet.

Analytical Sample Preparation

1. Gastric fluid samples

For analysis of samples from SGF, 0.5 ml of sample was placed in a test tube to which was added 30 µl of a mixture of 1 mg/ml Dex/Triamcinolone (TrAce) mixture (internal standard for calibration). Two ml of 100% ethanol were added followed by 150 µl of 0.2N NaOH solution to bring the pH to 5.0. The sample was mixed by repeated inversion before injecting onto the HPLC column for analysis of drug content.

2. Intestinal fluid samples

For analysis of samples from SIF, 0.5 ml of sample was transferred to a test tube to which was added 30 µl of a 1 mg/ml Dex/TrAce mixture. Two ml of 100% ethanol were then added and the sample mixed by repeated inversion before injection onto the HPLC column for analysis of drug content.

3. Colonic fluid samples

For analysis of samples from SCF, 150–500 mg of sample was added to a test tube and the mass was recorded. Thirty µl of a standard mixture of Dex and TrAce (1 mg/ml) was then added along with 2 ml water and 2 ml 100% ethanol. The mixture was then sonicated for 5 minutes and the coarse solids were removed by centrifugation. Resulting supernatants were transferred to a syringe and filtered through a 0.45 micron filter. The samples were mixed by repeated inversion prior to injection onto the HPLC column for analysis.

Hardness and friability testing was performed on the four dosage forms examined in drug release studies (prepared by premixing the Dex). The results are shown below in TABLE 3.

TABLE 3

| Formulation | Hardness (kp) (n = 7) | Friability (%) (n = 1) |
|---|---|---|
| C. | 14 ± 1 | 0.04 |
| D. | 2.2 ± 0.8 | 0.89 |
| A. | 4.5 ± 0.6 | 0.28 |
| B. | 3.6 ± 0.6 | 0.19 |

Drug Release

The results from three part dissolution testing systems provide the profile for drug release varied as a function of formulation. A tablet made from formulation C demonstrated "fast" release of the drug with approximately 90% of the Dex originally contained in the tablet being released into SGF by the 2 hour time point. This tablet significantly disintegrated in the presence of SGF. In contrast, the tablet prepared from formulations A, B and D showed very little release of drug until placed in SCF with the drug release profiles for tablets prepared from formulation A showing substantial drug release in SCF. Though a measurable amount of drug was detected in SCF, the majority of drug release from A, B and D tablets preferentially occurred in the presence of SCF. Complete disintegration of these tablets was observed in the SCF whereas very little disintegration was observed when immersed in SIF over the same time period.

On the basis of results obtained, formulations A, B and D are capable of releasing little if any drug in the stomach and small intestine while preferentially releasing drug in a sustained manner once the tablets reach the colon. Though total disintegration of the tablets was observed by 24 h, total release of Dex was not detected in these experiments. The stirring conditions in the SCF system were relatively mild; a likely explanation for these results, therefore, is that all the Dex was released from these dosage forms but not uniformly distributed throughout the viscous dissolution medium. The fast-releasing tablet releases drug primarily in the stomach and/or small intestine. This dosage form C provides a relatively rapid input of drug into the body as compared to the three other dosage forms. In addition to rapid drug release, C was observed to disintegrate completely in SGF within 1–2 hours.

Example 2

This example provides a pharmacoscintigraphic evaluation of the four formulations of Example 1 and shows the preferential release of the active ingredient, dexamethasone, into the colon from the three formulations of this invention. A study was designed to investigate the gastrointestinal transit and disintegration of the four formulations of Example 1 and to evaluate the subsequent absorption of dexamethasone released from the preparations. The study was a double blind, parallel group design in which blocks of eight healthy subjects received one of the four different formulations. Thirty-two healthy volunteers (18 male, 14 female) were administered tablets weighing approximately 333 mg each and containing approximately 2.7% dexamethasone (ie not more than 9 mg dexamethasone per tablet) made in accordance with Example 1. Each subject received a single tablet radiolabelled with $^{153}$Sm.

Clinical Supplies

Neutron activation methods were used to radiolabel dosage forms. These techniques require the addition of a stable isotope within a formulation; subsequent irradiation in a neutron source converts the isotope into a gamma emitting radionuclide. By using these neutron activation methods, exposure of workers to radiation can be minimized and complicated delivery systems can be labelled easily and efficiently. In order to validate this technique, the irradiation process must be shown to have no effect on the formulation, i.e. the preparation must behave in a similar manner both prior to and following the irradiation procedure. Dosage forms were irradiated for six minutes in a neutron flux of $10^{12}$n cm$^2$s$^1$ 48 hours prior to dosing and in vitro testing demonstrated that neither the addition of the samarium oxide nor the neutron activation process affected the performance of the dosage forms or the stability of the drug.

Dosing Details

The volunteers arrived fasted (from midnight) at the study site. Anterior and lateral anatomical markers containing 0.1 MfBq$^{99}$Tc$^m$ were taped to the skin over the right lobe of the liver. A single radiolabelied dosage form was administered to each of the volunteers at approximately 8:00 am with a 240 ml of water.

Anterior scintigraphic images were recorded at frequent intervals for up to 16 hours, using a gamma camera (General Electric Maxicamera) with a 40 cm field of view and fitted with a low energy parallel hole collimator. Images were recorded at approximately 10 minute intervals up to 12 hours post-dose and then at approximately 30 minute intervals until 16 hours post-dose. Return visits were made to the clinical unit at 24 and 36 hours post-dose to allow the acquisition of further images. Images were of 50 seconds duration for the first 9 hours after dosing but the acquisition time was then extended to 80 seconds until 16 hours post-dose. Images obtained at 24 and 36 hours post-dose were acquired for 120 seconds. The volunteer remained moderately active during the study period and all images were acquired with the subjects standing in front of the gamma camera. The images were recorded using a Bartec computer system and were stored on optical disk for subsequent analysis.

A standard light lunch, dinner and supper were provided at 4, 9 and 14 hours post-dose, respectively. Each subject drank 200 ml of water at two hours post-dose and fluids were allowed ad libitum after lunch. At the end of the study day 1, subjects were instructed to fast until returning to the clinical unit the following morning. Food was only allowed ad libitum after the 24 hour image and blood sample.

Blood Sampling

Venous blood samples (10 ml) were withdrawn via an intravenous cannual or by venepuncture according to the following time schedule:

0 (pre-dose), 1.0, 2.0, 4.0, 6.0, 8.0, 10.0, 12.0, 14.0, 16.0 24.0 and 36.0 hours post-dose The first 2 ml of blood withdrawn via the cannual was discarded and the subsequent 10 ml was withdrawn into serum separation monovettes. The cannulae were frequently flushed through with saline during the course of study day 1. The total amount of blood taken from each volunteer for the study, including pre- and post-study medical, was 190 ml.

The samples were left at room temperature for approximately 30 minute until a clot was formed. The samples were then centrifuged at approximately 3000 rmp (or 1800 g) for 7 minutes at 4° C. The resulting serum fraction was split into two aliquots by pipeting into two pre-labelled polypropylene screw cap tubes. Sample were flash frozen and then stored immediately at 20° C. A sample was subsequently shipped on dry ice to an assay center assay.

Scintigraphic Data Analysis

The data from the study were analyzed in line with pharmaceutical Profiles' Standard Operating Procedure for Quality Control of Gamma Camera Data Analysis to obtain the following parameters:

I. Gastric emptying time;
II. Small intestinal transit time; (a) Time of complete tablet disintegration and (b) anatomical location.
III. Colon Arrival time; (a) Time of initial tablet disintegration and (b) anatomical location.
IV. Transit histograms.

The recorded time of movement of the tablet from the stomach to the small intestine was taken as the mid-term between the times recorded for the two images about the transition. The times for colon arrival and initial and complete tablet disintegration were determined in the same manner. Small intestinal transit time was calculated by subtracting the gastric emptying time from the time at which initial colon arrival occurred. Initial tablet disintegration was defined as the time taken to detect signs of release of radioactive marker from the tablet in consecutive images while complete release was defined as the time at which all the radiolabel had dispersed within the gastrointestinal tract and no signs of a distinct 'core' remained.

Gastrointestinal Transit

The average gastric emptying time (I), average small intestinal transit time (II), and average colon arrival time (III), all given in minutes, are summarized in Table 4. As can be seen all of formulations A, B and D stayed intact long enough to reach the colon.

TABLE 4

| Gastrointestinal Transit Summary Formulation | | | |
|---|---|---|---|
| Formulation | I | II | III |
| A | 56 ± 42 | 258 ± 96 | 313 ± 89 |
| B | 33 ± 23 | 218 ± 33 | 251 ± 21 |
| C | (1) | (1) | (1) |
| D | 52 ± 43 | 243 ± 85 | 295 ± 73 |

(1) rapid disintegration prevented determination

Tablet Disintegration

The average initial tablet disintegration time in minutes (IV(a)) and anatomical location (IV(b)) and the average time for complete tablet disintegration in minutes (V(a)) and anatomical location (V(b)) are summarized in Table 5.

TABLE 5

| Tablet Disintegration Summary | | | | |
|---|---|---|---|---|
| Formulation | IV(a) | IV(b) | V(a) | V(b) |
| A | 104 ± 60 | UI | 472 ± 161 | C |
| B | 345 ± 138 | C | 741 ± 194 | C |
| C | 10 ± 17 | S | 125 ± 310 | S |
| D | 213 ± 97 | I | 734 ± 228 | C |

S = stomach;
C = colon;
I = intestine;
UI = upper intestine

Following administration of Formulations A, B, C and D initial tablet disintegration occurred on average at 104±60 minutes (range 40 to 227 minutes) post-dose, 345±138 minutes (range 174 to 630 minutes) post-dose, 10±17 (range 1 to 48 minutes) post-dose and 213±97 minutes (range 138 to 442 minutes) post-dose. Initial disintegration occurred in the stomach for each subject receiving Regimen C and also in the upper intestines for volunteers receiving Regimen A. In seven of the eight subjects that received Regimen D the tablets began to disintegrate in the small intestine whilst in subject 005, disintegration was only observed to commence after the tablet had reached the ascending colon. In six of the eight subjects who received Regimen B initial disintegration of the tablets was also observed following colon arrival. However, it was noted that a small amount of radioactive material 'leached' from each of the four formulations shortly after administration of the preparations. Initially this material was observed to disperse throughout the gastrointestinal tract, however, it could often not be detected in subsequent images. This material is thought to result from progressive erosion of the surface of the tablets due to the continual peristaltic action of the gut. For this reason, initial disintegration was recorded as the midpoint between the two images after which dispersed radioactive marker was observed in consecutive images.

Complete tablet disintegration was defined as the time at which all the radiolabel had dispersed within the gastrointestinal tract and no signs of a distinct 'core' remained. Complete tablet disintegration occurred on average at 472±161 minutes (range 305 to 769 minutes; n=8) post-dose, 741±194 minutes (399 to 934 minutes; n=8) post-dose, 125±310 minutes (range 1 to 829 minutes; n=7) post-dose and 724±228 minutes (range 354 to 892 minutes; n=5) post-dose for Regimens A, B, C and D respectively. Complete tablet disintegration was observed in the colon for each subject receiving Regimens A, B and D. Complete disintegration did not occur in the first 16 hours post-dose in three of the eight subjects who received Regimen D and, in the remaining five subjects who received this formulation, disintegration occurred distally. Complete disintegration was observed more proximally in the colon in those subjects receiving Regimens A and B with disintegration of Formulation B typically occurring more distal to that of Formulation A. Distribution of the radiolabel within the colon at 24 and 36 post-dose was typical for all four formulations and in line with previous scintigraphic studies.

Complete disintegration occurred in the stomach in six of the eight subjects receiving Regimen C. However, in subject 032 complete disintegration occurred in the ascending colon and disintegration must have occurred in the large bowel in subject 017 since radioactive marker was still apparent in the colon 24 hours after dosing. The reason for the dichotomy in the results for these two subjects receiving Regimen C is unclear, but may be that the rate of hydration of hydrophilic polymers is critical to the formation of a gel layer, which in turn determines the integrity properties of the actual tablet. It is possible that in 6 of the 8 subjects, the gel layer did not form quickly resulting in rapid tablet disintegration while in subjects 017 and 032 hydration of the polymer occurred rapidly, thereby significantly improving tablet integrity.

The scintigraphic data suggests that each of the four formulations behaved in a unique manner making it possible to distinguish between them. Formulation C showed early rapid release in the majority of cases. In three of the eight subjects who received Regimen D, complete disintegration of the tablets did not occur during the initial sixteen hour imaging period. In these cases complete release of the material occurred overnight and by virtue of the anatomical location of the marker at 24 hours post-dose, it could be concluded that release occurred somewhere in the large bowel. Release from Regimen A occurred more proximally in the large bowel while release from Regimen B occurred in the distal colon in five of the eight subjects who received this formulation.

Thus, formulations A, B and D (representative of compositions of this invention) all show preferential disintegration in the colon.

Example 3

By following the procedures of Example 1 but substituting the following compounds, similar compositions are prepared:

A. Budesonide
B. Fluticasone
C. Predisolone
D. Prednisone
E. Hydrocortisone

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

Example 4

This example explains a wet granulation method for preparing dexamethasone containing tablets according to the invention.

In this method, dexamethasone and PVP were co-dissolved in ethanol. This ethanolic mixture was added to guar gum drop-wise to form wet granules which were passed through a screen having a mesh size of number 18 then dried at 60° C. The dried granules were passed through screens with various mesh sizes and mixed with other ingredients such as HPMC and magnesium stearate. The resulting powder granule mixture was compressed into tablets.

In more detail, 0.174 grams of dexamethasone and 5.2 grams of PVP were codissolved in ethanol (Batch A used 50 ml and Batch B used 25 ml of ethanol). The ethanolic mixture was added to 100 grams of guar gum G3 dropwise, and mixed then sieved through a mesh number 18 and dried at 60° C until all ethanol was evaporated. The dried granules were sieved according to the following table:

TABLE 6

| The relationship between mesh # and particle diameter, $\mu$m | | | | | | |
|---|---|---|---|---|---|---|
| Mesh # | 30 | 40 | 60 | 120 | 140 | 200 |
| diameter | 600 | 425 | 250 | 125 | 106 | 75 |

The sieved granules were mixed with HPMC E3 and magnesium stearate in a V-shell blender for 10 minutes. This powder mixture was compressed manually into tablets by a rotary press (the weight of the tablets was 500 mg and the diameter of the punches 13/32") with a concave face. The formulation for each sub-batch was as follows:

| | | |
|---|---|---|
| HPMC E3 | 38.9% | 15.56 g |
| magnesium stearate | 0.5% | 0.20 g |
| dexamethasone | 0.1% | 0.04 g |
| PVP | 3.0% | 1.20 g |
| guar gum G3 | 57.5% | 23.00 g |
| Total | 100.0% | 40.00 g |

These tablets are useful in the process of this invention.

Example 5

This example sets forth a method for compression coating a core tablet with a composition comprising a hydrocolloid gum obtainable from higher plants and other pharmaceutically excipients. The process described may be adjusted to include an active ingredient in the core tablet.

A core tablet was made by mixing 79.5% lactose (Fast-Flo lactose), 20% Avicel PH-200 and 0.5% magnesium stearate in a V-blender for 10 minutes the mixed formulation was compressed using flat-faced punches (dia.=7 mm) on a Stokes B2 rotary tablet press. The weight of the tablet was adjusted to 175 mg/tablet and the hardness was maintained between 6–7 kP.

For the compression coating, 12.7 mm diameter concave punches were used. About one third (208 mg) of the total amount of guar gum composition (625 mg) was first placed in the die. The core tablet was then placed in the center on top of the guar gum layer. About 208 mg of the guar gum composition was then poured alongside the core tablet, followed by the remaining 208 mg as the top layer of the tablet. The tablet was then compressed and was dropped in deionized water for about 13 hours in a glass beaker with no shaking. After 13 hours a gel layer was formed around the tablet, which was swollen compared to its original size. When the tablet was split in half, the core was still found to be dry.

What is claimed is:

1. A pharmaceutical tablet having an inner composition optionally coated by a pharmaceutically-acceptable coating, said tablet designed for orally delivering a therapeutically effective amount of a drug to the lower GI tract without significant release of the drug in the upper GI tract after oral administration of the tablet, which inner composition of the tablet comprises
   about 0.01% by weight to about 10.0% by weight of a drug useful for treating a lower GI tract disorder;
   about 40% by weight to about 98% by weight of a hydrocolloid gum obtainable from higher plants; and
   about 2% by weight to about 50% by weight of a pharmaceutically acceptable excipient;
   no enteric polymeric material or gas-forming excipient, wherein the components of the inner composition are distributed so that the drug is concentrated in an active core with the gum and excipient surrounding the active core.

2. The tablet of claim 1, wherein said tablet is designed for orally delivering a therapeutically effective amount of a drug to the colon.

3. The tablet of claim 1, which is enterically coated.

4. The tablet of claim 3, wherein the drug is a corticosteroid.

5. The tablet of claim 4, wherein the corticosteroid is present in an amount of about 1% by weight to about 4% by weight of the inner composition.

6. The tablet of claim 5, wherein the corticosteroid is dexamethasone, budesonide, fluticasone, prednisone, prednisolone or hydrocortisone.

7. The tablet of claim 6, wherein the corticosteroid is micronized budesonide.

8. The tablet of claim 6 wherein the corticosteroid is micronized dexamethasone.

9. The tablet of claim 1, wherein the drug is 5-ASA.

10. The tablet of claim 1, wherein the drug is a peptide.

11. The tablet of claim 10, wherein the peptide is LHRH, growth hormone, vasopressin, insulin, calcitonin, glucagon, GHRH, relaxin, somatostatin, a cytokine or a lymphokine.

12. The tablet of claim 1, wherein the drug is a stimulant laxative.

13. The tablet of claim 12, wherein the drug is a bisacodyl.

14. The tablet of claim 1, wherein the hydrocofloid is guar gum, locust bean gum, gum tragacanth or karaya gum.

15. The tablet of claim 14, wherein the hydrocofloid is guar gum.

16. A method for treating a disorder of the lower GI tract in a human subject, which method comprises orally-administering to a human subject in need thereof a tablet of claim 1.

17. The method of claim 16, wherein the inner composition comprises
    about 0.5% by weight to about 5.0% by weight of a drug useful in treating a colonic disorder;
    about 50% by weight to about 70% by weight of a hydrocolloid gum obtainable from higher plants;
    about 25% by weight to about 50% by weight of the pharmaceutically-acceptable excipient.

18. The method of claim 16, wherein the disorder is characterized by inflammation of the colon and the drug is a corticosteroid.

19. The method of claim 18, wherein the corticosteroid is present in an amount of about 1% by weight to about 4% by weight.

20. The method of claim 19, wherein the corticosteroid is dexamethasone, budesonide, fluticasone, prednisone, prednisolone or hydrocortisone.

21. The method of claim 16, wherein the drug is 5-ASA.

22. The method of claim 16, wherein the hydrocolloid is guar gum, locust bean gum, gum tragacanth or karaya gum.

23. The method of claim 22, wherein the hydrocolloid is guar gum.

24. A method for preferentially delivering a drug to the lower GI tract wherein such drug is susceptible to enzymatic degradation in the upper GI tract, which method comprises orally-administering to a human subject in need thereof a tablet of claim 1.

25. The method of claim 24, wherein the drug is a peptide.

26. The method of claim 25, wherein the peptide is LHRH, growth hormone, vasopressin, insulin, calcitonin, glucagon, GHRH, relaxin, somatostatin, a cytokine or a lymphokine.

27. The method of claim 25, wherein the peptide is nafarelin, busarelin, goserelin, leuprolide, or a pharmaceutically-acceptable salt thereof and is delivered to treat endometriosis in a female human subject.

28. The method of claim 16, wherein the disorder is constipation and the drug is a stimulant laxative.

29. The method of claim 16, wherein the disorder is characterized by inflammation of the colon and the drug is 5-ASA.

30. The tablet of claim 10, wherein the peptide is selected from the group consisting of nafarelin, busarelin, goserelin, leuprolide, and a pharmaceutically-acceptable salt thereof.

* * * * *